United States Patent [19]

Belinka, Jr. et al.

[11] Patent Number: 5,495,042
[45] Date of Patent: Feb. 27, 1996

[54] NON-ALKALINE PURIFICATION OF AMINOPHOSPHONIC ACIDS

[75] Inventors: Benjamin A. Belinka, Jr., Kendall Park; Daniel J. Coughlin, Robbinsville, both of N.J.

[73] Assignee: Cytogen Corporation, Princeton, N.J.

[21] Appl. No.: 145,591

[22] Filed: Nov. 4, 1993

[51] Int. Cl.$^6$ .................................................. C07F 9/38
[52] U.S. Cl. ........................... 562/14; 540/474; 562/12
[58] Field of Search ........................ 562/12, 14; 540/474

[56] References Cited

U.S. PATENT DOCUMENTS

| | | | |
|---|---|---|---|
| 3,832,393 | 8/1974 | Krueger et al. | 260/502.5 |
| 3,956,370 | 5/1976 | Parry et al. | 260/502.5 |
| 3,959,361 | 5/1976 | Krueger et al. | 260/502.5 |
| 4,009,204 | 2/1977 | Krueger et al. | 260/502.5 |
| 4,012,440 | 3/1977 | Quinlan | 260/502.5 |
| 4,035,412 | 7/1977 | Quinlan | 260/502.5 |
| 4,937,333 | 6/1990 | Garlich et al. | 540/474 |
| 5,155,257 | 10/1992 | Kleiner | 562/15 |
| 5,159,108 | 10/1992 | Kieczykowski | 562/13 |

FOREIGN PATENT DOCUMENTS

| | | |
|---|---|---|
| 875501 | 7/1979 | Belgium . |
| 7900568 | 10/1979 | Brazil . |
| 202423 | 9/1983 | Czechoslovakia . |
| 0032338 | 7/1981 | European Pat. Off. . |
| 0225409 | 6/1987 | European Pat. Off. . |
| 2089675 | 7/1972 | France . |
| 2017974 | 11/1971 | Germany . |
| 2021148 | 11/1971 | Germany . |
| 2132511 | 1/1973 | Germany . |
| 2741504 | 3/1979 | Germany . |
| 164270 | 2/1989 | Ind. . |
| 57-75990 | 5/1982 | Japan . |
| 1230121 | 4/1971 | United Kingdom . |

OTHER PUBLICATIONS

Ault, "Techniques and Experiments for Organic Chemistry", 4th ed., Allyn & Bacon, Inc., Boston (1983), pp. 44–46, 50.
Inorganic Chemistry, vol. 22, 1983, pp. 1478–1482, E. N. Rizkalla, et al., "Nuclear Magnetic Resonance Study of Ethylenediaminetetrakis(methylenephosphonic acid) and Some Metal Complexes".
Phosphorus and Sulfur, 1983, vol. 16, pp. 233–238, Derek Redmore, et al., "Novel Magnetic N,N–bis(methylene)–bisphosponic Acids of α,ω–Diamines. Preparation and Characterization of [[(2–aminoethyl)imino]bis(methylene)]–bisphosphonic acid and [[(6–aminohexyl)imino]bis(methylene]–bisphosphonic acid".
Journal of Isotopes, vol. 5, No. 2, May 1992, pp. 72–76, Yang Zhi, et al., "Preparation of Yttrium–90 EDTMP for Bone Tumor Treatment", (abstract only).

Primary Examiner—José G. Dees
Assistant Examiner—Barbara S. Frazier
Attorney, Agent, or Firm—Lowe, Price, LeBlanc & Becker

[57] ABSTRACT

A process for the purification of aminophosphonic acids under non-alkaline conditions is described. In particular, aminophosphonic acids are slurred in neutral or acidic water, heated to reflux, cooled and then filtered. Product purities approaching 100% are thus obtained.

29 Claims, No Drawings

5,495,042

NON-ALKALINE PURIFICATION OF AMINOPHOSPHONIC ACIDS

BACKGROUND OF THE INVENTION

1. Field of the Invention

The present invention is directed to the purification of aminophosphonic acids More particularly, the present invention relates to the purification of aminophosphonic acid compounds, such as ethylenediamine tetra(methylene phosphonic acid) (EDTMP), 1,4,7,10-tetraazacyclododecane-1,4,7,10-tetra(methylene phosphonic acid) (DOTMP), diethylenetriamine penta(methylene phosphonic acid) (DTPMP), nitrilo tri(methylene phosphonic acid) (NTMP), hydroxyethylethylenediamine tri(methylene phosphonic acid) (HEEDTMP), tris(2-aminoethyl)aminehexa (methylene phosphonic acid) (TTHMP), and the like, by adding the crude, unpurified aminophosphonic acid to water at neutral or acidic pH to form a slurry that is then heated to reflux, cooled to approximately 80° C., and filtered.

2. Discussion of the Background

Aminophosphonic acids and their salts are well-known chelating agents for metal ions. Depending upon the properties of the metal ion to be complexed, the resulting metal-aminophosphonic acid complex may be used to treat tumors, to enhance a magnetic resonance image, a sonographic image, an X-ray image, and the like. Of course, aminophosphonic acid chelating agents are also useful in more traditional chelation technologies such as scale removal, water-softening, ore leaching, textile processing, food preservation, the treatment of lead poisoning, chemical analysis, and the like.

The preparation and use of aminophosphonic acids has been described. For example, Krueger et al. describe a process for producing aminoalkylene phosphonic acids by reacting alkylene glycol chlorophosphites with an aldehyde or ketone and an amine or an acid addition salt thereof or an acid amide of a lower mono- or dicarboxylic acid (see U.S. Pat No. 3,832,393, incorporated herein by reference). Garlich et al. disclose a method for purifying aminomethylenephosphonic acids for pharmaceutical use in which the aminomethylene phosphonic acid is dissolved in aqueous base, and the solution is added to an acid solution maintained at elevated temperature to precipitate the aminophosphonic acid (see U.S. Pat. No. 4,937,333, incorporated herein by reference).

As described above, aminophosphonic acids may be employed in therapeutic or pharmaceutical formulations. Thus, the purity of the aminophosphonic acid must be such that it is suitable for administration to humans. The production of pharmaceutical-grade products is an on-going and well-known problem in the pharmaceutical art, and the reduction and/or elimination of impurities from therapeutic or pharmaceutical products, including formulations, is a constant concern.

SUMMARY OF THE INVENTION

Accordingly, one object of this invention is to provide a novel process for purifying aminophosphonic acids.

Another object of this invention is to provide aminophosphonic acid-metal ion complexes that have been prepared with aminophosphonic acids purified according to the present inventive method.

Other objects of this invention and many of the attendant advantages thereof will become readily apparent by reference to the following detailed description of the preferred embodiments.

DETAILED DESCRIPTION OF THE PREFERRED EMBODIMENTS

The present invention is directed to a novel process for the non-alkaline purification of aminophosphonic acids, particularly ethylenediamine tetra(methylenephosphonic acid) (EDTMP), 1,4,7,10-tetraazacyclododecane-1,4,7,10-tetra(methylenephosphonic acid) (DOTMP), diethylenetriamine penta(methylenephosphonic acid) (DTPMP), nitrilotri(methylenephosphonic acid) (NTMP), hydroxyethyl ethylenediaminetri(methylenephosphonic acid) (HEEDTMP), tris(2-aminoethyl) aminehexa(methylenephosphonic acid) (TTHMP), and the like, wherein crude, unpurified aminophosphonic acid is added to water to form a slurry, which is heated to reflux, cooled to approximately 80° C., and filtered.

In the invention method, crude aminophosphonic acid is added to an amount of water from 2–4 times the amount of aminophosphonic acid (w/v) in a reaction vessel to form a slurry. The slurry is heated to reflux and stirred at reflux for between 1 and 48 hours. After refluxing, the slurry is cooled to approximately 70°–90° C., preferably 80° C. The cooled slurry is then filtered at approximately 70°–90° C., preferably 80° C. The product is then dried. If desired, the aqueous medium with which the aminophosphonic acid is slurried may be acidic. The pH of the slurry may fall in the range of less than about 1 to 7, preferably 1 to 2, most preferably 1.5.

The aminophosphonic acids, which may be purified by the invention method, are all well-known in the art, as are methods for their preparation. For example, U.S. Pat No. 4,937,333 and U.S. Pat No. 3,832,393 describe the preparation of aminophosphonic acids, including EDTMP, DOTMP, NTMP, and the like. In the present invention, the preferred method for preparing EDTMP is accomplished by first adding a 37% hydrochloric acid solution and phosphorous acid to a reaction vessel, followed by stirring until a homogenous solution is obtained. Ethylenediamine dihydrochloride is added to this homogenous solution, and the mixture is heated to reflux. Formaldehyde is added to the refluxing reaction mixture over a period of approximately 21 hours with concomitant production of the EDTMP, as a precipitate. If no precipitation is observed, a seed crystal may be added or other conventional methods employed to facilitate precipitation. After formaldehyde has been added and precipitation has begun, the reaction mixture is stirred at reflux for an additional 48 hours. The reaction mixture is then cooled to ambient temperature (approximately 20°–25° C.). The resultant slurry is stirred at room temperature for an additional 24 hours and filtered at room temperature. The crude, solid EDTMP obtained is washed with water and air dried.

In the invention purification method, the amount of water to which the crude aminophosphonic is added varies from approximately 1 to approximately 6 times (w/v) the amount of crude aminophosphonic acid, preferably 2 to 4 times. The water is either neutral (pH=7) or acidic (pH <7). Distilled and/or deionized water is preferred.

The crude aminophosphonic acid-water slurry is prepared by any method known in the art, for example, by stirring or shaking. Once the slurry is formed, it is heated with stirring to reflux (the reflux temperature is approximately 100° C., using water having a neutral pH, and may be higher, using water having an acidic pH). The refluxing slurry is then continuously stirred for a period of about 1 to about 96 hours, preferably 24 to 72 hours, most preferably 48 to 72 hours.

After being stirred at reflux, the aminophosphonic acid-water slurry is cooled. Preferably, the slurry is cooled to between 70° and 90° C., more preferably 75°–85° C., most preferably 80° C. Next, the slurry is filtered at approximately the temperature to which it has been allowed to cool to obtain purified aminophosphonic acid. However, the slurry may also be filtered at reflux temperature, or the slurry may be cooled to room temperature and filtered at room temperature.

Filtration of the slurry may be accomplished by any means known in the art. For example, filtration through a Buchner funnel, or the like, may be employed. Drying of the filtered, purified aminophosphonic acid may similarly be accomplished by any known technique. For example, the purified aminophosphonic acid may be dried in a vacuum oven, on a buchner funnel attached to a water aspirator, or the like method.

The degree of purity of the aminophosphonic acids purified by the invention process may be monitored or determined by any number of conventional techniques, including $^{31}P$ NMR, HPLC (with use, e.g., of a refractive index detector), and the like. Typical purities obtained with the invention process approach 100%, and are generally greater than 98%. The invention process always provides a product that is more pure than the starting crude aminophosphonic acid.

While the above description of the preferred embodiments more than adequately sets out the present invention, the same will be illustrated further by the following nonlimiting Examples.

EXAMPLE 1

Preparation of EDTMP.

331.2 ml of 37% hydrochloric acid and 208.5 g of phosphorous acid were added to a 2000 ml reaction vessel. This mixture of acids was stirred until a homogenous solution was obtained and then approximately 73.15 grams of ethylenediamine dihydrochloride was added thereto. The mixture was heated to reflux and 262.6 g of 37% formaldehyde was added thereto over a period of 21 hours. After the addition of formaldehyde had been completed and precipitation had begun, the reaction mixture was stirred at reflux for an additional 48 hours and then cooled to ambient temperature (20°–25° C.). The room temperature slurry was then further stirred at room temperature for an additional 23 hours. The slurry was filtered and the filter cake was washed with 500 ml of water. The filter cake was air dried for 24 hours using a water aspirator. Yield of crude EDTMP=193.7 g (77.6%). The material obtained was 96.6% pure as determined by HPLC using Refractive Index (R.I.) detection. $^{31}P$ NMR indicated this material to be 96.4% EDTMP. HPLC analysis was run using an Anion Exchange Chromatography column, 100 mm×4.6 mm. Mobile phase was 8 mM sulfuric acid solution; flow rate was 2 ml/min. A Waters 410 refractive index detector was used. $^{31}P$ NMR spectra were run in a mixture of $D_2O/H_2O/NaOH$ on a 360 MHz spectrometer.

EXAMPLE 2

Purification of EDTMP.

Twenty-five grams of the crude EDTMP prepared above was added to a 250 ml reaction vessel, and 100 ml of water (pH=5.5) was added thereto to obtain a slurry. The slurry was then heated with stirring until reflux was reached. Heating under reflux was continued for 1 hour. The heated, refluxing slurry was then allowed to cool to 80° C., and the solids present in the reaction flask were filtered at this temperature. The precipitates were then air dried on a Buchner funnel for 2.5 hours to yield 14.76 g (59%) of purified EDTMP. The purity of the material was 98.9% as determined by HPLC using R.I. detection. $^{31}P$ NMR indicated this material to be 99.0% EDTMP.

EXAMPLE 3

Purification of EDTMP.

Twenty grams of crude EDTMP prepared by the method of Example 1, above, were added to a 250 ml reaction vessel, and water (78.2 ml, pH=5.5) was added thereto to obtain a slurry. The slurry was then heated with stirring until reflux was reached and refluxing was continued for 48 hours. The heated, refluxing slurry was allowed to cool to 80° C. and filtered at this temperature. The solid precipitates were then dried on a Buchner funnel using a water aspirator for 2 hours. Yield of EDTMP=12.4 g (62%). The purity of this material was 99.1% as determined by HPLC using R.I. detection. $^{31}P$ NMR indicated this material to be 98.9% EDTMP.

EXAMPLE 4

Purification of EDTMP.

Twenty grams of crude EDTMP prepared as in Example 1, above, were added to a 250 ml reaction vessel, and 75 ml of 4.6N HCl was added thereto to form a slurry. The slurry was heated with stirring until reflux was reached and refluxing was continued for approximately 2 hours. The heated, refluxing solution was then cooled to 80° C. and seeded with 0.1 g of a purified sample of EDTMP and allowed to stir for an additional 2 hours at 80° C. The resultant precipitates were then filtered (at 80° C.) and dried on a Buchner funnel using a water aspirator for 2 hours. Yield of EDTMP filter cake=8.85 g (44%). The purity was 99.1% as determined by HPLC using R.I. detection. $^{31}P$ NMR indicated this material to be 99.3% EDTMP.

EXAMPLE 5

Purification of DOTMP.

20 grams of crude DOTMP, prepared by the method of Garlich, J. R., et. al., U.S. Pat. No. 4,937,333, is combined with 78.2 ml of water at pH 5.5 to form an aqueous slurry. The mixture is heated with stirring to reflux and stirred at reflux temperature for 48 hours. Afterwards, the mixture is allowed to cool to about 80° C., filtered at that temperature, and allowed to dry on a Buchner funnel using a water aspirator. The DOTMP obtained is more pure than the starting crude material by $^{31}P$ NMR and HPLC analysis.

Likewise, the purification of DTPMP, NTMP, HEEDTMP, and TTHMP is accomplished in the manner illustrated above with similar results.

EXAMPLE 6

Preparation of EDTMP.

331.2 ml of 37% hydrochloric acid and 208.5 g of phosphorous acid were added to a 2000 ml reaction vessel. This mixture of acids was stirred until a homogenous solution was obtained and then approximately 73.15 grams of ethylenediamine dihydrochloride was added thereto. The mixture was heated to reflux and 262.6 g of 37% formaldehyde was added thereto over a period of 5 hours. After the addition of formaldehyde had been completed and precipitation had begun, the reaction mixture was stirred at reflux for an additional 20 hours and then cooled to 78° C. The hot slurry was then filtered and the filter cake was washed with 250 ml of water. The resultant white granular product was then dried under vacuum to give 165 g of crude EDTMP. Yield of crude EDTMP was 66.1%. The material obtained was 96.0% pure by HPLC using Refractive Index (R.I.) detection. $^{31}$P NMR indicated this material to be 97.0% EDTMP.

EXAMPLE 7

Purification of EDTMP.

Ten grams of the crude EDTMP prepared according to Example 6, above, was added to a 250 ml reaction vessel, and 37.5 ml of 4.6N hydrochloric acid was added thereto to obtain a slurry. The slurry was then heated with stirring until reflux was reached. Heating under reflux was continued for 2 hours. The heated, refluxing slurry was then allowed to cool to 25°–30° C. and the solids present in the reaction flask were filtered at this temperature. The precipitates were dried on the Buchner funnel using a water aspirator for 1.5 hours to yield 7.52 g (75.2%) of purified EDTMP. The purity of this material was 99.1% as determined by HPLC using R.I. detection. $^{31}$P NMR indicated this material to be 99.1% EDTMP.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the non-alkaline purification of an aminophosphonic acid compound comprising:
   a) combining a previously prepared aminophosphonic acid compound of a given purity and water having a neutral or acidic but not alkaline pH to form a slurry;
   b) heating said slurry to reflux;
   c) maintaining said slurry at reflux for a period of time in the range of about 1 to about 96 hours; and
   d) filtering said slurry of step (c) at or below reflux temperature to obtain an aminophosphonic acid compound of greater purity than said previously prepared aminophosphonic acid compound.

2. The process of claim 1, wherein said aqueous mixture has a neutral pH.

3. The process of claim 1, wherein said aqueous mixture has an acidic pH.

4. The process of claim 1, wherein said aminophosphonic acid compound is selected from the group consisting of EDTMP, DOTMP, DTPMP, NTMP, HEEDTMP, and TTHMP.

5. The process of claim 1, wherein the aminophosphonic acid compound is DTPMP.

6. The process of claim 1, wherein the aminophosphonic acid compound is NTMP.

7. The process of claim 1, wherein the aminophosphonic acid compound is HEEDTMP.

8. The process of claim 1, wherein the aminophosphonic acid compound is TTHMP.

9. The process of claim 1, in which said aqueous mixture of step (c) is allowed to cool to a temperature below reflux prior to performing step (d).

10. The process of claim 9, wherein the temperature below reflux ranges from about 70° to about 90° C.

11. The process of claim 10, wherein the temperature below reflux is about 80° C.

12. The process of claim 1, wherein the filtration of said aqueous mixture is carried out at a temperature ranging from about 70° to about 90° C.

13. The process of claim 12, wherein the filtration of said aqueous mixture is carried out at a temperature of about 80° C.

14. A process for the non-alkaline purification of EDTMP comprising:
   a) combining a previously prepared EDTMP of a given purity and water having a neutral or acidic but not alkaline pH to form a slurry;
   b) heating said slurry to reflux;
   c) maintaining said slurry at reflux for a period of time in the range of about 1 to about 96 hours; and
   d) filtering said slurry of step (c) at or below reflux temperature to obtain EDTMP of greater purity than said previously prepared EDTMP.

15. A process for the non-alkaline purification of DOTMP comprising:
   a) combining a previously prepared DOTMP of a given purity and water having a neutral or acidic but not alkaline pH to form a slurry;
   b) heating said slurry to reflux;
   c) maintaining said slurry at reflux for a period of time in the range of about 1 to about 96 hours; and
   d) filtering said slurry of step (c) at or below reflux temperature to obtain DOTMP of greater purity than said previously prepared DOTMP.

16. The process of claim 1, in which step (c) is maintained for up to 72 hours.

17. The process of claim 1, in which step (c) is maintained for up to 48 hours.

18. The process of claim 1, in which step (c) is maintained for up to 24 hours.

19. The process of claim 14, in which step (c) is maintained for up to 48 hours.

20. The process of claim 15, in which step (c) is maintained for up to 48 hours.

21. A process for the non-alkaline purification of an aminophosphonic acid compound comprising:
   a) combining a previously prepared aminophosphonic acid compound of a given purity and water having an acidic, not alkaline, pH to form a slurry;
   b) heating said slurry to reflux;
   c) maintaining said slurry at reflux for a period of time in the range of about 1 to about 96 hours; and
   d) filtering said slurry of step (c) at or below reflux temperature to obtain an aminophosphonic acid compound of greater purity than said previously prepared aminophosphonic acid compound.

22. A process for the non-alkaline purification of an aminophosphonic acid compound comprising:
   a) combining a previously prepared aminophosphonic acid compound of a given purity and water having a neutral or acidic but not alkaline pH to form a slurry;
   b) heating said slurry to reflux; and
   c) filtering said slurry of step (b) at or below reflux temperature to obtain an aminophosphonic acid compound of greater purity than said previously prepared aminophosphonic acid compound.

23. The process of claim 22 which further comprises stirring said slurry at reflux for a period of time prior to said filtering step.

24. The process of claim 23 in which said slurry is stirred at reflux for about 1 hour.

25. The process of claim 23 in which said slurry is stirred at reflux for about 24 hours.

26. The process of claim 22 in which said aminophosphonic acid compound is selected from the group consisting of EDTMP, DOTMP, DTPMP, NTMP, HEEDTMP or TTHMP.

27. The process of claim 22 in which said aminophosphonic acid compound is EDTMP.

28. The process of claim 23 in which said aminophosphonic acid compound is EDTMP.

29. The process of claim 22 in which said water has an acidic pH.

* * * * *